United States Patent
Amiri

Patent Number: 5,888,202
Date of Patent: Mar. 30, 1999

[54] UNI-ROOT MULTI-EXIT HAIR IMPLANT

[76] Inventor: Ahmad Amiri, 15 Wertheim Ct. #708, Richmond Hill, Canada, L4B 3H7

[21] Appl. No.: 718,497
[22] PCT Filed: Mar. 24, 1995
[86] PCT No.: PCT/CA95/00168
§ 371 Date: Jul. 11, 1997
§ 102(e) Date: Jul. 11, 1997
[87] PCT Pub. No.: WO95/28133
PCT Pub. Date: Oct. 26, 1995

[30] Foreign Application Priority Data

Apr. 15, 1994 [CA] Canada ................................. 2121398

[51] Int. Cl.⁶ ................................................... A61F 2/10
[52] U.S. Cl. ..................... 623/15; 606/187; 132/53; 132/201
[58] Field of Search ........................ 623/11, 15; 606/9, 606/187, 228; 132/53, 56, 201, 273; 607/89

[56] References Cited

U.S. PATENT DOCUMENTS

| | | | |
|---|---|---|---|
| 3,003,155 | 10/1961 | Mielzynski et al. | 623/15 |
| 3,596,292 | 8/1971 | Erb | 623/15 |
| 3,699,969 | 10/1972 | Allen | 606/187 |
| 3,831,202 | 8/1974 | Hulsen | 623/15 |
| 4,103,365 | 8/1978 | Applegate | 606/187 |
| 4,751,927 | 6/1988 | Yamada | 606/187 |
| 4,768,517 | 9/1988 | Joachim | 623/15 |
| 4,944,751 | 7/1990 | Santi | 623/15 |
| 5,061,284 | 10/1991 | Laghi | 623/15 |
| 5,137,533 | 8/1992 | Giampapa | 623/15 |

FOREIGN PATENT DOCUMENTS

| | | | |
|---|---|---|---|
| 2372621 | 8/1978 | France | 623/15 |
| 2529074 | 12/1983 | France | |
| 2809327 | 4/1979 | Germany | 606/187 |
| 3435608 | 5/1986 | Germany | |
| 8703804 | 6/1987 | Germany | |

*Primary Examiner*—Paul B. Prebilic
*Assistant Examiner*—Bruce E. Snow

[57] ABSTRACT

Synthetic hair may be implanted using bundles of synthetic fibres joined at their lower end so that they will be firmly anchored in the scalp and not easily pulled out. The implants may be inserted by a tool which comprises a short sharp hollow tube and a manipulating handle. The tip of the tube may be inserted into the scalp to provide a conduit into which the synthetic fibres are sewn into the scalp.

The synthetic fibres are implanted by having curved needles at one end and a juncture of several fibres at the other end. The needles are inserted through the tube and into the scalp and out through the outer surface at various locations like normal hair, but because they are joined and anchored within the scalp, will not be easily removed. Alternatively, the skin can be surgically lifted and the fibre inserted through the skin from underneath.

10 Claims, 2 Drawing Sheets

UNI-ROOT MULTI-EXIT HAIR IMPLANT

This invention uses the transmission Ahmad Amiri (Inventor) patent application to Canadian Intellectual Property Office, file No. 2,121,398 filed 15th Apr. 1994 and application to World Intellectual Property Organization, Patent Cooperation Treaty, file No. PCT/CA95/00168 dated 24th Mar. 1995.

FIELD OF INVENTION

This invention is a hair implant and methods of implanting it in the skin with or without lifting the skin, that may be used in treatment of baldness, thin hair or undesirable hair.

DESCRIPTION OF RELATED ART

Current remedies for baldness include:

Wigs: which may be loose or fixed to natural hair or glued to skin. Their drawbacks are artificial appearance, subject to accidental dislodging, sweat retaining hence less hygienic, and that can't help thin hair.

Surgical shrinking of bald skin: and stretching the hairy skin to replace it. Drawbacks are severe limitation, evasiveness, high cost and no use for thin or undesirable hair.

Transplant: from hairy to bald areas. Drawbacks being shortage of donor area, no guarantee of successful or continued regrowth of donor hair in host skin, high cost, lengthy treatment for several months and sparse looking hair as final result.

Chemical treatments: best of which is Rogain (monoxidil) is only marginally successful for only some people. Any improvement is reversed once treatment is halted. It is costly and can't help undesirable hair.

Implant: U.S. Pat. No. 4,103,365 titled "Method of implanting synthetic hair". In this method one or more synthetic hair fibres are knotted together at 10" intervals. Then the bundle is attached to a suturing needle which is inserted into the skin and pulled through the skin and out of the skin such that all knots are out of the skin except for the one furthest from the needle which is let to remain embedded in the skin.

Then the process is repeated leaving the second furthest knot from needle under the skin and so on until all knots are inside the skin serving as anchors keeping the bundle in place. Then the portions of the bundle which are outside the skin are cut midway between each two consecutive knots. The end result is many holes on the skin from each one bundle of several fibres emerging out of skin, each two bundle is anchored by one bulky knot under the skin.

Drawbacks of U.S. Pat. No. 4,103,365 (method of implanting synthetic hair) are:

1- It relies primarily on the knot for fixing the bundle in the skin, but pulling some or all fibres in the bundle will pull the knot out through the same tunnel in the skin which was created at implantation and kept open by the same bundle.

2- Several fibres exit the skin from each hole created on the skin. Gaps between cylindrical adjacent hairs cannot be closed up by the surrounding skin as the outer fibres closest to the perimeter of the hole prevent the skin to close in.

3- Each hole created on the skin is large, having to let many fibres in or out, hence more difficult to heal and being covered, and that in the middle part of each whole there are triangular openings between bundled fibres that render the skin to influx of infection.

4- Method requires that each knot, which is purposefully large to provide better anchorage, is pulled through the skin many times. For example a bundle of 10 knots would require 55 passages of knots into, through and out of the skin, extremely damaging to the skin tissue.

5- Several fibres exiting same point on the skin does not resemble natural hair.

6- Each knot large enough to hold 2 respective bundles, under the skin creates an unsightly 'pimple' on the scalp. Thousands of knots necessary to cover a bald head would be uncomfortable, unsightly, and possibly unhealthy.

7- This method has proven unsuccessful in tests, partly due to above reasons.

Uni-Root Multi-Exit Hair Implant is fundamentally different from U.S. Pat. No. 4, 103,365, as will be explained in the forthcoming disclosure, in particular:

a) The common juncture that lies under the skin does not have any bulky knot, but is preferably same thickness as one fibre, entering the skin only once, never exiting the skin, hence causing little damage to tissue and no pimple on the scalp.

b) Each fibre is inserted into and pulled out of the skin individually, emerging from its individual exit point, which is different from several fibres sharing passage. In particular, the skin can easily heal around one single fibre leaving no open gap.

c) There is no need to run many bulky knots, each through several points and tunnels in the skin, causing serious damage to tissue.

d) Each fibre is attached to one respective needle, making it possible for each fibre to exit the skin from its unique point which is different from all fibres attached to same needle.

e) Implanting is assisted by a hollow sharp short tube to guide needles and fibres through the skin and reduce skin contact with inserted needles and fibres, resulting in less damage to tissue, which is different from forcing knotted bundles of fibres through the tissue.

f) Several other differences of this invention and prior art are inferred from the description

SUMMARY OF THE INVENTION

Overcoming the drawbacks of prior art and other advantages are to be achieved by the present invention which provides hair implant in which each fibre is rooted under the skin and comes out separately like natural hair, can have desired thickness, colour, density, curl, length, or direction, may be made of strong material to withstand all pressures and be long lasting, is easy to mass produce, is easy to implant by trained but non-medical practitioners, can remedy thinning hair and replace undesirable hair, as well as overcoming baldness.

These features are sought to be presented by a synthetic hair implant comprising a plurality of synthetic fibres joined together at one end and a needle suitable for penetrating human skin at the other end of each fibre.

Preferably a bundle or group of fibres are joined together at a common juncture at one end and each has a curved skin penetrating needle at its other end.

These fibres may be implanted with the aid of an apparatus comprising a sharp tube capable of penetrating the skin and having an inlet opening and an outlet opening through which the fibres may be inserted into the scalp. Preferably the devise also has a handle so that it may be manipulated and inserted into the skin.

The synthetic hair implants may be placed using the implanting apparatus by the method of the present invention in which the needles at one end of the synthetic fibres are inserted through the inlet opening of the tube, after it has been penetrated into the scalp, and emerge at the outlet end of the tube into the scalp and then pass through the outer surface of the skin until the lower end is drawn into the skin layer and the fibres protrude like hair, after which they can be cut off at the desired length. A bundle of fibres all joined at one end and each having a needle attached at the other end, can be inserted throught a single placement of the tube tip in the same manner.

BREIF DESCRIPTION OF THE DRAWINGS

The present invention may be better understood by a description of one embodiment thereof with reference to the attached drawings in which.

Figure 1:
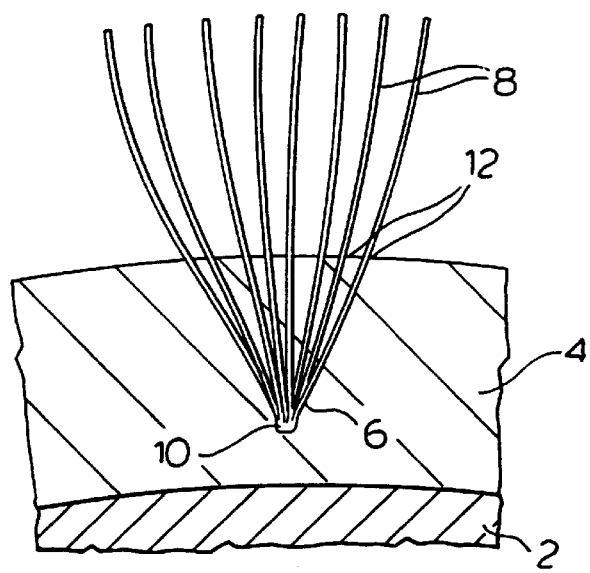
FIG. 1 is a cross-sectional view of an implant in accordance with the present invention.

In the illustrated embodiment FIG. 1 shows a cross section in which the skull 2 is overlain by the skin of the scalp 4 and has implanted therein a bundle 6 comprising several synthetic fibres 8 which constitute part of a synthetic hair replacement.

Fibres 8 are joined together at the juncture 10 by fusing, welding, casting or cutting sheets of material to desired shape, or other means depending on the nature of the material which makes up the strands.

It will be appreciated that because the implant has several strands emerging at different locations 12 on the surface of the scalp from a single juncture 10, it will be rather difficult for any of the strands 8 or the entire bundle 6 to be removed from the scalp by any of the normal forces, such as combing, brushing, or abrasion on a pillow or hat.

As contemplated for purposes of this invention, the synthetic strands 8 should be thin, strong, compatible with the human body and chemistry, smooth, flexible, erect, weldable (or otherwise capable of being fastened together at their lower end to form the juncture 10). It should also be capable of being coloured or dyed, and in all considerations of appearance be as similar to hair as possible. For instance, Kevlar or Optical Glass fibres may be typical of materials which satisfy these needs.

Figure 2:
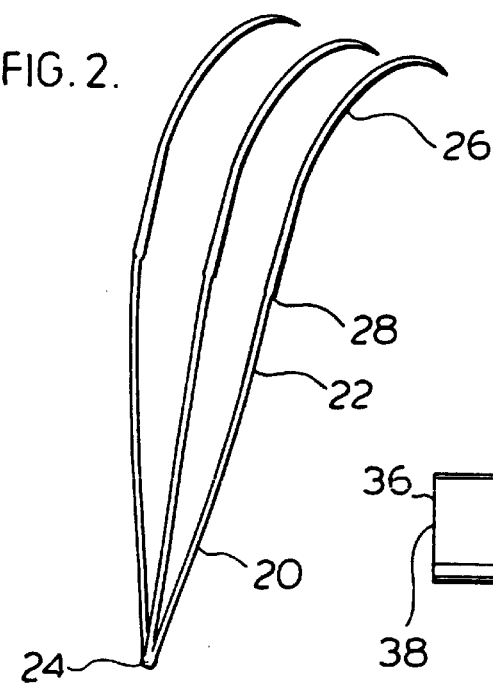
FIG. 2 is an elevation view of an implant apparatus with means for inserting it.
Figure 3:
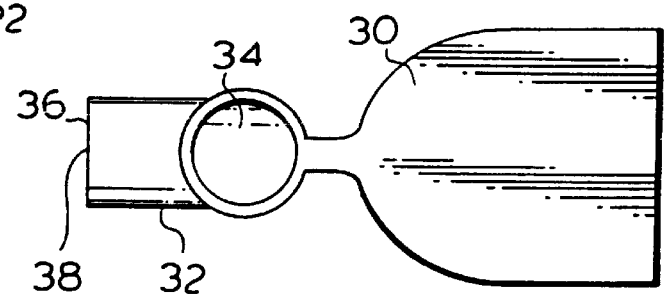
FIG. 3 is a plan view of an instrument for inserting an implant of the present invention.

FIG. 2 illustrates a bundle 20 of synthetic hairs 22 similar to the bundle illustrated in FIG. 1, but for ease of illustration only three strands are shown. The strands are joined at the juncture 24 by welding or similar means (preferably without any appreciable increase in size or thickness), and have, each of them, at the opposite ends a curved needle 26 suitable for penetrating the skin, although the needle should be adapted to connect to the fibre at a smooth joint 28 so that the needles and fibres can be easily passed through the skin in a manner to be described later. FIG. 3 illustrates a device used in the implanting technique of the present invention and includes a handle 30 with a skin penetrating tube 32 having an inlet opening 34 and an outlet opening 36. The illustrated tube may be short and is designed with a sharp tip 38 capable of easily and efficiently penetrating the skin without unnecessary damage.

Figure 4:
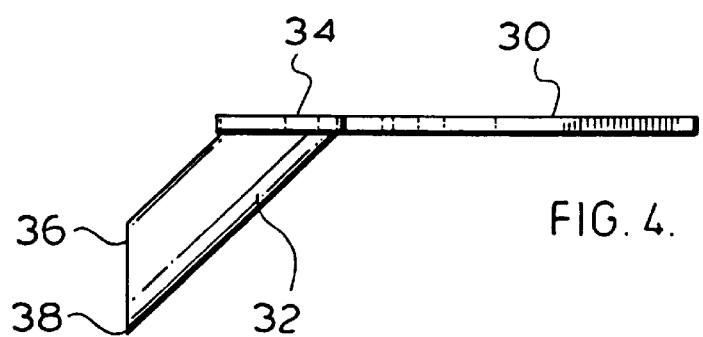
FIG. 4 is a sectional view of an instrument for inserting an implant of the present invention.

FIG. 4 is an elevation view of the instrument in FIG. 3. It should be realized that it will be very short, in the order of the thickness of the scalp (unless a longer stem is desired to penetrate along the layer of skin).

Figure 5:
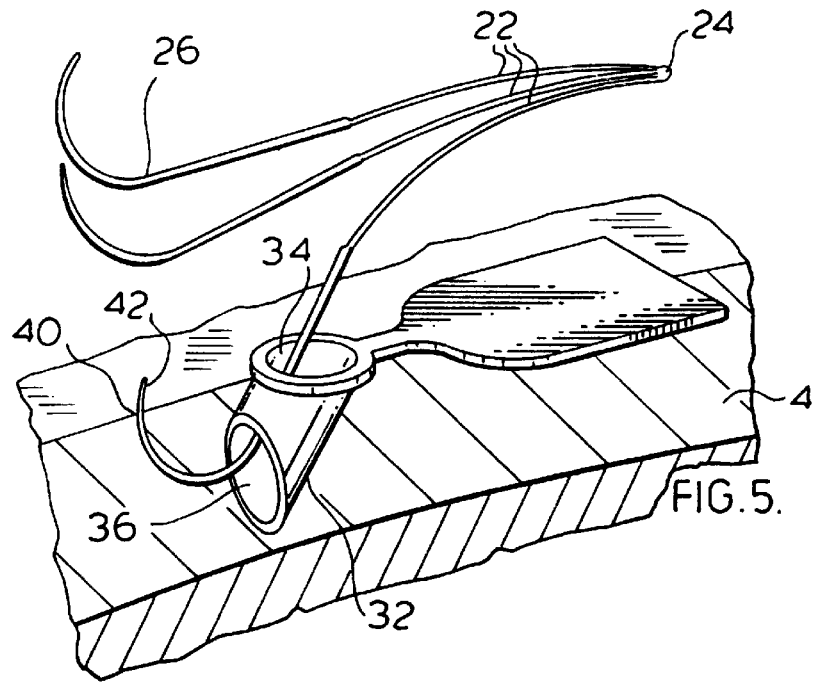
FIG. 5 is a cross section showing the procedure for placing an implant of the present invention.

FIG. 5 is a cross-section of a scalp similar to that illustrated in FIG. 1 and shows the method by which the present invention is employed. The instrument shown in FIG. 3 and 4 is illustrated with the tube 32 implanted in the skin of the scalp 4 with the inlet opening 34 exposed and the outlet opening 36 embedded in the skin. A bundle of synthetic hair fibres, as illustrated in FIG. 2, having attached needles 26, is also shown with one of the needles having been partially inserted by entering the opening 34, passing through the tube 32, out the opening 36, and out of the surface of the skin at 40.

It will be appreciated that the protruding needle 42 can be further drawn until the attached fibre emerges from the scalp, and each of the other needles 26 can be inserted, because of their curved nature, in the same manner, temporarily leaving the juncture outside the tube.

Figure 6:
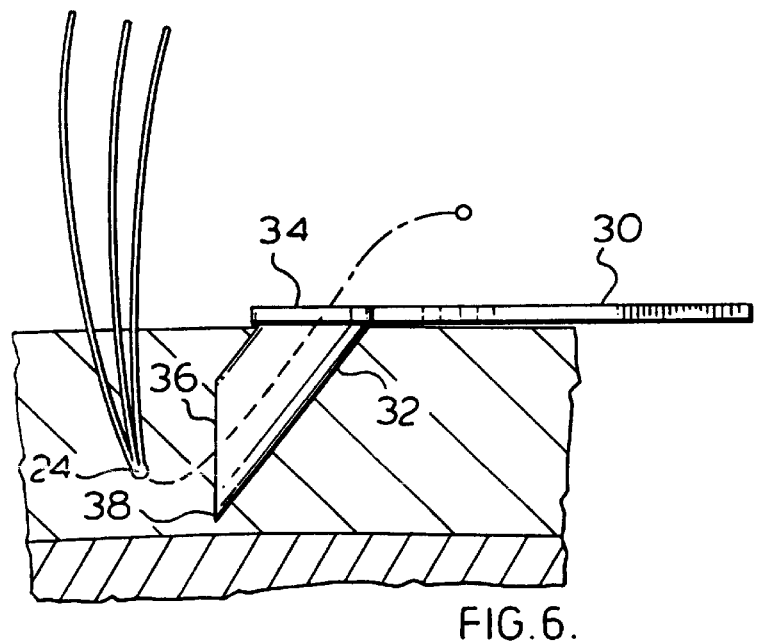
FIG. 6 is a vertical section showing the placement of an implant.

As illustrated in FIG. 6, when all of the needles have been inserted through the scalp and out again, the fibres can be drawn through until the juncture 24 emerges from the outlet 36 of the tube at which point the tube may be removed and used for another implant in an adjacent location.

The fibres of the bundle will emerge from the scalp at separate locations around the tube, but because they are joined at their juncture 24, will be relatively firmly secured in place and will not be easily pulled out by usual activities, such as combing or brushing. At the end of an implant, of course, the needles are cut off. When all of the implants are in place, the new synthetic hair is trimmed.

Because the individual fibres emerge from individual locations on the scalp, the bundle will have a relatively natural looking pattern. Furthermore, because the fibres are synthetic, they can be of whatever desired thickness, colour, density, curl, length, or flexibility desired, and can even be implanted with a predetermined direction.

The fibres of the present invention are capable of automatic and mass production and the technique may be employed with a minimum of skill by trained non-medical practitioners. The implants are permanent, fixed, washable, maintenance free, and substantially identical to one's own hair. In fact it is considered part of the present invention that it may be used not only to treat baldness but to remedy thinning hair as a supplement, or to replace hair that is considered undesirable or unattractive.

Chemical removal of regrown natural hair may be employed without harmfully affecting the synthetic implants.

Although the foregoing describes a technique which requires no surgeon or hospital, it is of course possible to use the synthetic bundle of fibres as shown in FIG. 1, and implant them directly through the scalp using a surgical technique to lift the skin and penetrate from the inside by an incision, preferably using straight needles. This, however, would likely involve in-patient treatment whereas the application described using the tube and curved needles would require no surgeon or surgery room.

If for some reason it was desired to remove the hair implanted by this method, it can be done by selecting one fibre from each bundle and shaving the other off as close to the scalp as possible. The bundle can then be pulled out by the one remaining fibre. Of course it is necessary to know which fibres belong to which bundle, and in order to facilitate this, it is possible to manufacture the fibres so that each bundle has one in which there is some code ( 54,56, 58,60 ) which would identify one fibre from the others in a single bundle .

Figure 7:
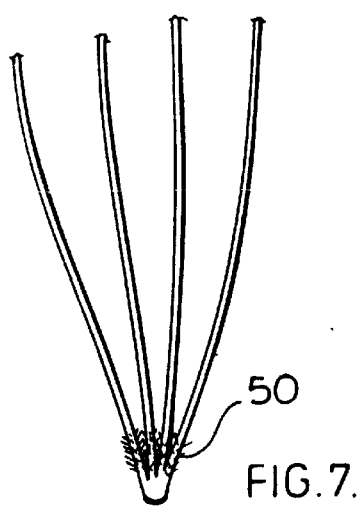
FIG. 7 is a close up view of a modified version of the implant of FIG. 1.

A modified version of an implant is shown in FIG. 7 in which the portion of the fibres near the juncture are formed with barbs as illustrated at 5 so as to further reduce the likelihood that they can be pulled out.

It will, of course, be appreciated that numerous modifications and variations of the illustrated embodiment may be employed without departing from the inventive concept herein.

DESCRIPTION OF THE PREFERRED EMBODIMENTS (S)

The most important features of our invention are the "common juncture" which remains under the skin and several fibres that emerge from the skin, "each fibre" from a "different point" on the skin. Each fibre is attached to one respective needle as a means of implanting, needles to be trimmed after implanting. Therefore numerous methods of constructing the implant and implanting it may be devised all relying on same inventive concept.

The invention utilizes, as an aid to implanting method, a device, being a short tube, with a sharp lower outlet opening and an upper inlet opening, which upper opening surrounded by a rim attached to a handle means of manipulating the device. Such device seems to be the subject of Patent "FR-A-2,529,074" (Instrument Permentant l'Implantation de Greffons de Cuir Chevelu). This invention does not claim such device as part oft he invention, but uses it as a desirable but not essential tool for one of the two primary methods of implanting.

The embodiments of the invention in which an exclusive property or privilege is claimed are defined as follows:

1. Hair implant comprising several fibres, all fibres having one common juncture at a bottom end, and each of the fibres has at its opposite end one respective curved needle, suitable for penetrating human skin, attached to it at a smooth joint.

2. Hair implant as in claim (1) in which some or all of the fibres are formed with barbs over a portion of the fibre that is near the common juncture.

3. Hair implant as in claim (1) in which one of the fibres is coded on a section which is intended to be outside the skin, so as to distinguish it from other fibres of the same implant.

4. Hair implant as in claim (2) in which one of the fibres is coded on a section which is intended to be outside the skin, so as to distinguish it from other fibres of the same implant.

5. Hair implant comprising several fibres, all fibres having one common juncture at a bottom end, and each fibre has at it's opposite end one respective needle, suitable for penetrating skin, attached to it at a smooth joint.

6. Hair implant as in claim (5) in which some or all of the fibres are formed with barbs over a portion of the fibre that is near the common juncture.

7. Hair implant as in claim (5) in which one of the fibres is coded on a section which is intended to be outside the skin, so as to distinguish it from other fibres of the same implant.

8. Hair implant as in claim (6) in which one of the fibres is coded on a section which is intended to be outside the skin, so as to distinguish it from other fibres of same implant.

9. A method of implanting a hair implant in the skin, without lifting the skin, which implant is made of several fibres with a common juncture at a bottom end and each fibre attached to one respective curved skin penetrating needle at another end, using a hair implanting device comprising a hollow tube having a sharp skin penetrating lower outlet opening and an upper inlet opening surrounded by a rim preventing the upper inlet opening to enter the skin, which rim is attached to a handle for manipulating the tube, such that when the lower outlet opening is inserted into the skin to the desired depth, the upper inlet opening and the rim rest touching the surface of the skin, the tube is inside the skin communicating the inlet and outlet openings, and the handle is outside the skin without blocking the upper inlet opening, which method comprising steps of:

inserting said tube's sharp tip lower outlet opening into the skin to the desired depth;

inserting each of the curved needles of the hair implant through the upper inlet opening and out of the lower outlet opening of the said tube, and then out of the surface of the skin at a unique exit point other than the exit points of other needles, all exit points being at the proximity of the said tube upper inlet opening, all along ensuring that the common juncture of the implant does not enter said tube until all needles of the hair implant have been through the tube and out of the skin;

pulling all the needles away from the skin so as to move the common juncture of the implant into the skin via the upper inlet opening of the tube, through the tube to the lower outlet opening of the tube, remaining embedded in an under layer of the skin;

removing the tube out of the skin;

trimming the needles off the implanted fibres.

10. A method of implanting hair implants in a skin, each implant comprising several fibres with a common juncture at a bottom end and each fibre attached to one respective skin penetrating needle at another end, which method comprising the steps of:

surgically lifting said skin, inserting all the needles of the hair implant through the skin from the underside of the lifted skin, and out of the surface of the skin such that each needle exits the skin at a point unique to that needle;

pulling all needles away from the surface of the skin so as to move the common juncture of the hair implant close and attached to the under side of the skin;

repeating above steps for all other implants that are intended for the lifted skin;

replacing lifted skin and stitching or adhering it back;

trimming the needles off the inserted fibres.

\* \* \* \* \*